(12) United States Patent
Greenberg et al.

(10) Patent No.: US 6,858,220 B2
(45) Date of Patent: Feb. 22, 2005

(54) IMPLANTABLE MICROFLUIDIC DELIVERY SYSTEM USING ULTRA-NANOCRYSTALLINE DIAMOND COATING

(75) Inventors: Robert J. Greenberg, Los Angeles, CA (US); Brian V. Mech, Sherman Oaks, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 404 days.

(21) Appl. No.: 10/046,458

(22) Filed: Oct. 26, 2001

(65) Prior Publication Data

US 2002/0119176 A1 Aug. 29, 2002

Related U.S. Application Data

(60) Provisional application No. 60/272,962, filed on Feb. 28, 2001.

(51) Int. Cl.$^7$ ................................................ A61F 2/02
(52) U.S. Cl. ...................................................... 424/423
(58) Field of Search ................................. 424/422, 423

(56) References Cited

U.S. PATENT DOCUMENTS

| | | | |
|---|---|---|---|
| 4,991,582 A | * | 2/1991 | Byers et al. |
| 5,750,926 A | | 5/1998 | Schulman et al. |
| 5,797,898 A | | 8/1998 | Santini, Jr. et al. |
| 6,123,861 A | | 9/2000 | Santini, Jr. et al. |
| 6,527,762 B1 | | 3/2003 | Santini, Jr. et al. |
| 6,551,838 B2 | | 4/2003 | Santini, Jr. et al. |

OTHER PUBLICATIONS

D.M. Zhou, et al., "Accelerated Corrosion Tests on Silicon Wafer for Implantable Medial Devices", Proc. of 198th Electrochemical Society Meeting, 363, Oct. 2000.
D.M. Gruen, "Nanocrystalline Diamond Films" Annu. Rev. Mater. Sci., 29 211–59 (199).
D.M. Gruen, et al. "Buckyball Microwave Plasmas: Fragmentation and Diamond Film Growth", J. Appl. Phys., 75 (3) 1758–63 (1994).

* cited by examiner

*Primary Examiner*—Carlos Azpuru
(74) *Attorney, Agent, or Firm*—Gary Schnittgrund

(57) ABSTRACT

An implantable biocompatible microchip drug delivery substrate is coated with a thin film of ultra-nanocrystalline diamond; assuring that the device is biocompatible and impermeably sealed, to prevent the substrate from being dissolved by the living tissue and to protect the drugs from premature release or undesired reaction with the body fluids. The coating is selectively patterned by doping to create electrically conductive areas that can be used as an electrically activated release mechanism for drug delivery. The conformal ultra-nanocrystalline diamond coating uniformly covers the device, providing relief from sharp edges and producing a strong, uniformly thick impermeable coating around sharp edges and on high aspect-ratio parts. The ultra-nanocrystalline diamond coating provides a conformal coating on the biocompatible device, which is of approximately uniform thickness around sharp corners and on high aspect-ratio parts. The conformal nature of the coating assures impermeability and strength despite the presence of difficult to coat shapes.

28 Claims, 1 Drawing Sheet

IMPLANTABLE MICROFLUIDIC DELIVERY SYSTEM USING LTRA-NANOCRYSTALLINE DIAMOND COATING

CROSS REFERENCE TO RELATED APPLICATION

This application claims the benefit of U.S. Provisional Application Ser. No. 60/272,962, filed on Feb. 28, 2001.

FIELD OF THE INVENTION

The present invention relates to a microfluidic delivery system that is coated with an inert and impermeable thin film and more particularly to controlled time of release and rate of release, single and multi-welled drug delivery devices, which may also be implantable.

BACKGROUND OF THE INVENTION

Implantable microfluidic delivery systems, as the microchip drug delivery devices of Santini, et al. (U.S. Pat. No. 6,123,861) and Santini, et al. (U.S. Pat. No. 5,797,898) or fluid sampling devices, must be impermeable and they must be biocompatible. The devices must not only exhibit the ability to resist the aggressive environment present in the body, but must also be compatible with both the living tissue and with the other materials of construction for the device itself. The materials are selected to avoid both galvanic and electrolytic corrosion.

In microchip drug delivery devices, the microchips control both the rate and time of release of multiple chemical substances and they control the release of a wide variety of molecules in either a continuous or a pulsed manner. A material that is impermeable to the drugs or other molecules to be delivered and that is impermeable to the surrounding fluids is used as the substrate. Reservoirs are etched into the substrate using either chemical etching or ion beam etching techniques that are well known in the field of microfabrication. Hundreds to thousands of reservoirs can be fabricated on a single microchip using these techniques.

The physical properties of the release system control the rate of release of the molecules, e.g., whether the drug is in a gel or a polymer form. The reservoirs may contain multiple drugs or other molecules in variable dosages. The filled reservoirs can be capped with materials either that degrade or that allow the molecules to diffuse passively out of the reservoir over time. They may be capped with materials that disintegrate upon application of an electric potential. Release from an active device can be controlled by a preprogrammed microprocessor, remote control, or by biosensor. Valves and pumps may also be used to control the release of the molecules.

A reservoir cap can enable passive timed release of molecules without requiring a power source, if the reservoir cap is made of materials that degrade or dissolve at a known rate or have a known permeability. The degradation, dissolution or diffusion characteristics of the cap material determine the time when release begins and perhaps the release rate.

Alternatively, the reservoir cap may enable active timed release of molecules, requiring a power source. In this case, the reservoir cap consists of a thin film of conductive material that is deposited over the reservoir, patterned to a desired geometry, and serves as an anode. Cathodes are also fabricated on the device with their size and placement determined by the device's application and method of electrical potential control. Known conductive materials that are capable of use in active timed-release devices that dissolve into solution or form soluble compounds or ions upon the application of an electric potential, including metals, such as copper, gold, silver, and zinc and some polymers.

When an electric potential is applied between an anode and cathode, the conductive material of the anode covering the reservoir oxidizes to form soluble compounds or ions that dissolve into solution, exposing the molecules to be delivered to the surrounding fluids. Alternatively, the application of an electric potential can be used to create changes in local pH near the anode reservoir cap to allow normally insoluble ions or oxidation products to become soluble. This allows the reservoir cap to dissolve and to expose the molecules to be released to the surrounding fluids. In either case, the molecules to be delivered are released into the surrounding fluids by diffusion out of or by degradation or dissolution of the release system. The frequency of release is controlled by incorporation of a miniaturized power source and microprocessor onto the microchip.

One solution to achieving biocompatibility, impermeability, and galvanic and electrolytic compatibility for an implanted device is to encase the device in a protective environment. It is well known to encase implantable devices with glass or with a case of ceramic or metal. Schulman, et al. (U.S. Pat. No. 5,750,926) is one example of this technique. It is also known to use alumina as a case material for an implanted device as disclosed in U.S. Pat. No. 4,991,582. Santini, et. al. (U.S. Pat. No. 6,123,861) discuss the technique of encapsulating a non-biocompatible material in a biocompatible material, such as poly(ethylene glycol) or polytetrafluoroethylene-like materials. They also disclose the use of silicon as a strong, non-degradable, easily etched substrate that is impermeable to the molecules to be delivered and to the surrounding living tissue. The use of silicon allows the well-developed fabrication techniques from the electronic microcircuit industry to be applied to these substrates. It is well known, however, that silicon is dissolved when implanted in living tissue or in sa ine solution.

SUMMARY OF THE INVENTION

An implantable microfluidic delivery system is coated with a thin film coating, about one-micron thick, of ultra-nanocrystalline diamond; thereby assuring that the device is biocompatible and impermeably sealed. The impermeable seal prevents the substrate from dissolving due to contact with living tissue. The conformal ultra-nanocrystalline diamond coating uniformly covers the device, providing relief from sharp edges and producing a strong, uniformly thick impermeable coating around sharp edges and on high aspect-ratio parts. The conformal nature of the coating helps assure impermeability and strength despite the presence of difficult to coat shapes.

When employed as an ultra-nanocrystalline diamond cover on the drug-containing reservoir, the coating may be designed to be removable by application of an electric current. The coating is selectively patterned by doping to create electrically conductive areas that are used as an electrically activated release mechanism for drug delivery and that are electrical conductors which carry electric current to electrodes to initiate the electrically activated release mechanism.

OBJECTS OF THE INVENTION

It is an object of the invention to provide an ultra-nanocrystalline diamond coated microchip drug delivery substrate that is impermeably sealed and inert for implantation in a living body.

It is an object of the invention to provide an ultra-nanocrystalline diamond coated microchip drug delivery substrate that has a uniform thickness coating around corners such that the coating maintains its impermeable sealing capability.

It is an object of the invention to provide an ultra-nanocrystalline diamond coated microchip drug delivery substrate that has electrically conductive areas that are patterned to provide a mechanism for electrically activated drug release.

Other objects, advantages and novel features of the present invention will become apparent from the following detailed description of the invention when considered in conjunction with the accompanying drawing.

DETAILED DESCRIPTION OF THE PREFERRED EMBODIMENTS

Figure 1:
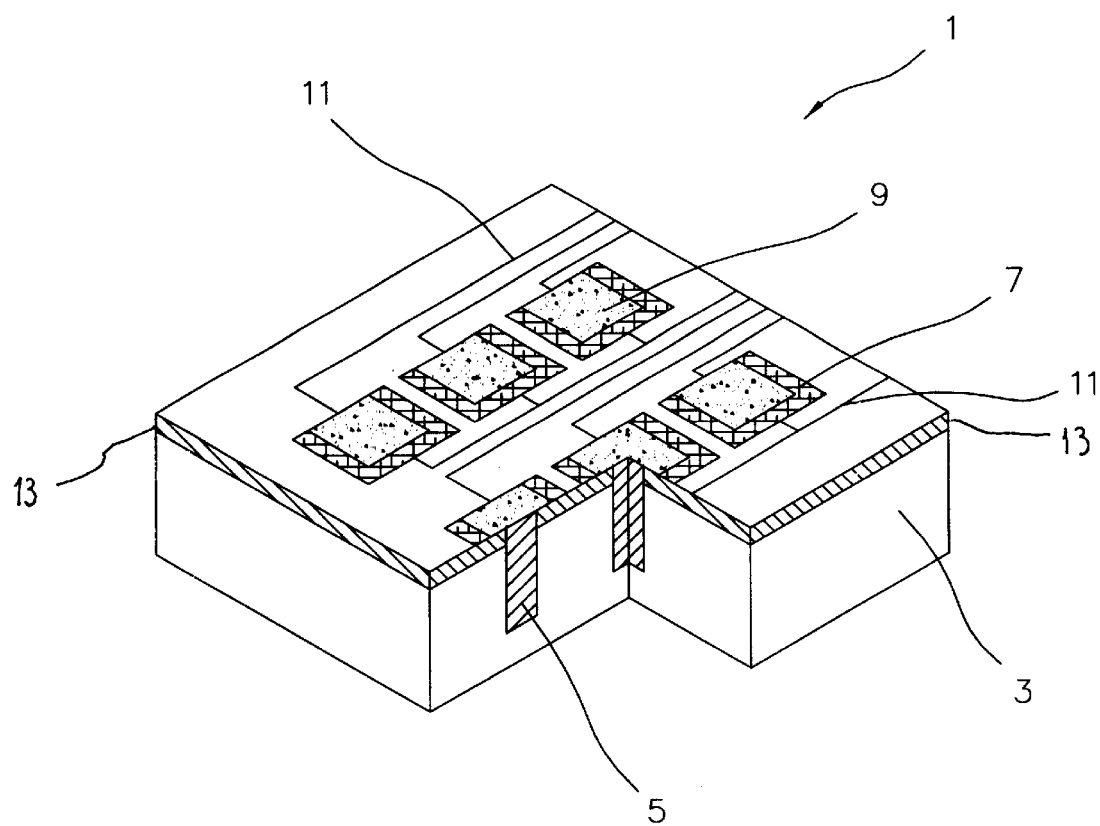
FIG. 1 illustrates a perspective view of the microchip drug delivery device.

Implantable microchip fluid delivery devices generally are comprised of a microchip 1, as shown in FIG. 1. The microchip 1 must be biocompatible and impermeable to assure that the drug or other molecule 5 contained in the reservoirs of the substrate 3 are protected from the living tissue of the body and to retain the drug or other molecule 5 until the desired release time.

It is known to fabricate reservoirs, by conventional microchip techniques, in the substrate of the delivery device from silicon. Silicon is dissolved when exposed, long term, to living tissue in a living body, unless coated with a biocompatible coating. An ultra-nanocrystalline diamond (UNCD) coating 13 exhibits excellent mechanical, electrical, and electrochemical properties. Using a thin film coating deposition process, such as that disclosed by Gruen and Krauss (U.S. Pat. No. 5,772,760), yields a coating that is inherently low in porosity, electrically non-conductive and biocompatible. U.S. Pat. No. 5,772,760 is incorporated herein by reference in its entirety. Coatings as thin as 40 nm have demonstrated excellent impermeability properties. The UNCD thin film coating 13 is conformal when applied to complex or high aspect-ratio shapes.

Characteristics of this UNCD coating 13 that make it particularly well suited to the present invention are:

uniform morphology resulting in a very high bulk density, highly conformal and able to cover very high-aspect ratio features uniformly, electrical properties can be controlled by varying the deposition parameters, so as to make selected areas electrically conductivity, low-temperature deposition thereby avoiding damage to electrical and passive components, and easily patternable via selective seeding, photolithography, or oxygen etching.

Unique UNCD coating 13 properties are not all present in any other single coating candidate for microchip drug delivery devices. Candidate coatings include conventional chemical vapor deposited diamond thin films, diamond-like carbon, or SiC. However, none of these coatings offers impermeability in thin coatings that are applied at low temperature and that are deposited by a none-line-of-sight method, as does UNCD. The UNCD coating 13 possesses these characteristics:

(a) extremely low surface roughness (20–30 nm), approximately independent of film thickness up to approximately 10 $\mu$m thickness;

(b) extremely good conformality when deposited on high aspect-ratio features;

(c) extremely low coefficient of friction;

(d) high hardness, fracture toughness, flexural strength, and wear life, (e) low electrical conductivity, but can be doped to become conductive, and (f) excellent resistant to degradation in living tissue environments.

The UNCD coating 13 consists primarily of phase pure randomly oriented diamond crystallites. UNCD coatings are grown using a microwave plasma chemical vapor deposition technique involving a $C_{60}$/Ar or $CH_4$/Ar chemistry, which provides $C_2$ dimers as the main growth species that insert directly into the growing diamond lattice with a low energy barrier. The limited amount of atomic hydrogen in the plasma leads to a very high re-nucleation rate (~$10^{11}$ cm$^{-2}$ sec$^{-1}$). This results in the UNCD coatings 13 with 2 to 5 nm grain size and 0.4 nm grain boundaries that provide the unique properties described herein. In addition, the low activation energy for $C_2$ species incorporation into the growing film yields the UNCD coating 13 at temperatures as low as approximately 350° C. This temperature is very low compared to many conventional coating processes, such as glass encapsulation or chemical vapor deposition.

Miniaturized drug delivery devices that are implanted in a living body benefit from a UNCD coating 13 that, in addition to biocompatibility, corrosion resistance, and impermeability, can be patterned to form electrically conductive electrodes. Patterning is done by selective doping of the UNCD coating 13 to convert the normally electrically insulating UNCD 13 to an electrical conductor. The electrical conductors 11 are formed in this manner, as is the anode electrode reservoir cap 9. These electrode caps 9 are formed as covers on the drug 5 or other molecule-containing reservoirs. Upon application of an electric current along the electrical conductors 11, through the cathode electrodes 7 and into the anode electrode reservoir cap 9 anode electrode reservoir cap 9 disintegrates to expose the drug or other molecule 5 to the living tissue, thus allowing the drug or other molecule 5 to enter the body. It is obvious that the device may equally well be used to deliver reagents or to act as a diagnostic agent in addition to delivering drugs.

The inert nature of a very thin coating of UNCD 13 was demonstrated by the present inventors. A silicon substrate coated with 40 nm of UNCD coating 13 was exposed to silicon etchant having a composition of 67% $HNO_3$ and 33% HF, by volume. The etchant was placed drop-wise on the UNCD coating 13, where it was allowed to stand at 60° C. for one-hour. The coating had been unaffected when observed microscopically at 1000× after this exposure.

Therefore, the UNCD coating 13 may be used as part of a biocompatible and impermeable microchip drug delivery packaging process to isolate the substrate 3, which is typically silicon, and to isolate the drug or other molecule 5 from the tissue and fluids that are present in the living tissue. In this manner, the substrate 3 is protected from attack by the living tissue and the drug or other molecule 5 is maintained free from attack by either the silicon or the living tissue.

The UNCD coating 13 on an integrated circuit is "conformal", which means that the coating has a uniform thickness as the coating follows the contours of the device. Achieving a conformal coating on high aspect-ratio parts and around sharp corners on these devices is a particular challenge for thin films that are deposited by other means. UNCD coating 13 uniformly covers all aspects of the intricately machined substrate 3 including the multiplicity of reservoirs.

Obviously, many modifications and variations of the present invention are possible in light of the above teachings. It is therefore to be understood that, within the scope of the appended claims, the invention may be practiced otherwise than as specifically described.

What is claimed is:

1. A microfluidic delivery system for the transport of molecules comprising:
    a substrate;
    a reservoir in said substrate for containing the molecules;
    a fluid control device controlling release of said molecules from said reservoir; and
    a thin film inert impermeable coating applied to said substrate.

2. The microfluidic delivery system according to claim 1 wherein—said thin film inert impermeable coating is biocompatible.

3. The microfluidic delivery system according to claim 1 wherein—the molecules are comprised of drugs.

4. The microfluidic delivery system according to claim 1 wherein—said thin film inert impermeable coating is comprised of ultra-nanocrystalline diamond.

5. The microfluidic delivery system according to claim 1 wherein—said thin film inert impermeable coating is comprised of ceramic.

6. The microfluidic delivery system according to claim 5 wherein—said thin film inert impermeable coating is applied by ion-beam assisted deposition.

7. The microfluidic delivery system according to claim 5 wherein—said ceramic is comprised of alumina.

8. The microfluidic delivery system according to claim 5 wherein—said ceramic is comprised of zirconia.

9. The microfluidic delivery system according to claim 1 wherein—said fluid control device is a permeable cap.

10. The microfluidic delivery system according to claim 1 wherein
    said fluid control device is a disintegrating cap.

11. The microfluidic delivery system according to claim 9 wherein
    said cap is comprised of electrically conductive ultra-nanocrystalline diamond.

12. The microfluidic delivery system according to claim 1 wherein
    said fluid control device is a pump.

13. The microfluidic delivery system according to claim 12 wherein
    said pump is an electrostatic pump.

14. The microfluidic delivery system according to claim 12 wherein
    said pump is an electromagnetic pump.

15. The microfluidic delivery system according to claim 12 wherein
    said pump is a pneumatic pump.

16. The microfluidic delivery system according to claim 12 wherein
    said pump is a piezoelectric pump.

17. The microfluidic delivery system according to claim 1 wherein
    said fluid control device is a valve.

18. The microfluidic delivery system according to claim 17 wherein
    said valve is an electrostatic valve.

19. The microfluidic delivery system according to claim 17 wherein
    said valve is an electromagnetic valve.

20. The microfluidic delivery system according to claim 17 wherein
    said valve is a pneumatic valve.

21. The microfluidic delivery system according to claim 17 wherein
    said valve is a piezoelectric valve.

22. The microfluidic delivery system according to claim 1 wherein
    said substrate is comprised of silicon.

23. A microfluidic delivery system for the release of molecules comprising:
    a substrate;
    at least one reservoir in the substrate that is suitable to contain the molecules;
    the reservoir having a reservoir cap positioned on the reservoir over the molecules;
    wherein release of the molecules from the reservoir is controlled by said reservoir cap; and wherein
    wherein said substrate is coated with a thin film of ultra-nanocrystalline diamond deposited on said biocompatible device wherein said thin film forms a biocompatible impermeably sealed substrate.

24. The microfluidic delivery system according to claim 23 wherein
    said molecules are released by diffusion through said reservoir cap.

25. The microfluidic delivery system according to claim 23 wherein
    said molecules are released by disintegration of said reservoir cap.

26. The microfluidic delivery system according to claim 23 wherein
    said substrate is comprised of silicon.

27. The microfluidic delivery system according to claim 23 wherein
    said reservoir cap is comprised of a thin film of ultra-nanocrystalline diamond.

28. The microfluidic delivery system according to claim 27 wherein
    at least a portion of said ultra-nanocrystalline diamond thin film is electrically conductive.

* * * * *